US010478269B2

(12) United States Patent
Jin

(10) Patent No.: US 10,478,269 B2
(45) Date of Patent: Nov. 19, 2019

(54) METHOD FOR AUTOMATICALLY MOVING OBJECT IN SIMULATION SYSTEM AND SIMULATION SYSTEM USING THE SAME

(71) Applicants: DIORCO CO., LTD., Suwon-si, Gyeonggi-do (KR); Yong-Kyu Jin, Hwaseong-si, Gyeonggi-do (KR)

(72) Inventor: Yong-Kyu Jin, Hwaseong-si (KR)

(73) Assignee: DIRCO CO., LTD., Suwon-si (KR)

( * ) Notice: Subject to any disclaimer, the term of this patent is extended or adjusted under 35 U.S.C. 154(b) by 0 days.

(21) Appl. No.: 15/535,048

(22) PCT Filed: Jul. 7, 2015

(86) PCT No.: PCT/KR2015/007012
§ 371 (c)(1),
(2) Date: Jun. 10, 2017

(87) PCT Pub. No.: WO2016/093455
PCT Pub. Date: Jun. 16, 2016

(65) Prior Publication Data
US 2017/0348071 A1    Dec. 7, 2017

(30) Foreign Application Priority Data
Dec. 11, 2014 (KR) .................. 10-2014-0178446

(51) Int. Cl.
*A61C 7/00* (2006.01)
*G06T 19/20* (2011.01)

(52) U.S. Cl.
CPC .............. *A61C 7/002* (2013.01); *A61C 7/00* (2013.01); *G06T 19/20* (2013.01); *A61C 2007/004* (2013.01)

(58) Field of Classification Search
CPC ..... A61C 7/002; A61C 2007/004; A61C 7/00; G06F 17/5009; G06M 11/00; G07C 9/00; G06T 19/20
(Continued)

(56) References Cited

U.S. PATENT DOCUMENTS 5,431,562 A * 7/1995 Andreiko ............ A61C 7/00
433/24
5,602,891 A * 2/1997 Pearlman ............ A61B 6/463
250/363.01
(Continued)

FOREIGN PATENT DOCUMENTS

JP      2012096427 A    5/2012
KR   1019910006874 A   4/1991
(Continued)

OTHER PUBLICATIONS

English translation of Korean Office Action dated May 22, 2016 in Korean Patent Application No. 10-2014-0178446 (Notice of Rejection), 6 pg.
(Continued)

*Primary Examiner* — Rehana Perveen
*Assistant Examiner* — Justin C Mikowski
(74) *Attorney, Agent, or Firm* — Ichthus International Law PLLC

(57) ABSTRACT

The present invention relates to a method for automatically moving an object in a simulation system, and a simulation system using the same. The method for automatically moving an object in a simulation system includes: moving a first object of a plurality of objects in a first direction; measuring a vector distance between the first object and a second object which is an object adjacent to the first object according to the movement of the first object; and automatically vector-moving the second object by a predetermined distance in the
(Continued)

first direction along a preset path so that the vector distance is in a preset vector distance range.

12 Claims, 6 Drawing Sheets

(58) Field of Classification Search
 USPC .............................................................. 703/6
 See application file for complete search history.

(56) References Cited

U.S. PATENT DOCUMENTS

| | | | | |
|---|---|---|---|---|
| 6,744,914 | B1* | 6/2004 | Rubbert ................... | A61C 7/00 345/419 |
| 7,134,874 | B2* | 11/2006 | Chishti .................... | A61C 7/00 |
| 9,937,023 | B2* | 4/2018 | Andersson ......... | A61C 13/0004 |
| 2002/0015934 | A1* | 2/2002 | Rubbert ................... | A61C 7/00 433/29 |
| 2007/0087302 | A1* | 4/2007 | Reising .................. | A61C 7/145 433/24 |

FOREIGN PATENT DOCUMENTS

| | | |
|---|---|---|
| KR | 1020050042043 A | 5/2005 |
| KR | 1020050082526 A | 5/2006 |
| KR | 101132080 B1 | 4/2012 |
| KR | 101138354 B1 | 4/2012 |
| KR | 101218388 B1 | 1/2013 |
| KR | 101413222 B1 | 6/2014 |

OTHER PUBLICATIONS

English translation of Korean Office Action dated May 30, 2016 in Korean Patent Application No. 10-2014-0178446 (Notice of Allowance), 4 pg.

International Search Report (ISR) dated Sep. 21, 2015 in PCT/KR2015/007012, 3 pgs.

* cited by examiner

METHOD FOR AUTOMATICALLY MOVING OBJECT IN SIMULATION SYSTEM AND SIMULATION SYSTEM USING THE SAME

CROSS-REFERENCE TO RELATED APPLICATION(S)

This application is the National Stage entry of the International Application No. PCT/KR2015/007012, filed on Jul. 7, 2015, claiming priority to Korean Patent Application No. 10-2014-0178446, filed on Dec. 11, 2014, the contents of which are incorporated herein by reference in their entirety.

TECHNICAL FIELD

The present invention relates to a method for automatically moving an object in a simulation system capable of improving convenience of a user by automatically moving an adjacent object in the case in which objects overlap with each other or move, and a simulation system using the same.

BACKGROUND ART

Computer aided engineering (CAE) has been used in order to support engineers in many works. For example, in a structure or product design procedure, a CAE analysis, particularly, a finite element analysis (FEA) has been often used in order to evaluate responses (for example, stress, displacement, and the like) under various loading conditions (for example, a static or dynamic condition).

Recently, various simulation apparatuses for such a computer aided engineering technology have been developed, and these simulation apparatuses have been used in a computer graphic (CG) work in movie shooting, a virtual experiment in the medical practice, or the like, as well as study fields of science technology.

In such a simulation, when a user moves one object depending on a specific purpose in a state in which a plurality of objects exist, all of the objects related to the moving object should manually move, which is troublesome in the simulation.

DISCLOSURE

Technical Problem

An object of the present invention is to provide a method for automatically moving an object in a simulation system capable of improving convenience of a user by automatically moving an adjacent object depending on a specific condition in the case in which an object moves, and a simulation system using the same.

Technical Solution

According to an exemplary embodiment of the present invention, a method for automatically moving an object in a simulation system may include: moving a first object of a plurality of objects in a first direction; measuring a vector distance between the first object and a second object which is an object adjacent to the first object according to the movement of the first object; and automatically vector-moving the second object by a predetermined distance in the first direction along a preset path so that the vector distance is in a preset vector distance range.

The automatic vector-moving of the second object may include deciding that the first object and the second object overlap with each other to separation-vector-move the second object along a movement direction of the first object in order to allow the first object and the second object to be in a preset range, when the vector-movement distance is a minus value.

The automatic vector-moving of the second object may include deciding that the first object and the second object are spaced apart from each other to adjacent-vector-move the second object along a movement direction of the first object in order to allow the first object and the second object to be in the preset vector distance range, when the vector-movement distance is a plus value.

The method for automatically moving an object in a simulation system may further include automatically moving a third object which is an object adjacent to the second object so that the third object is in the preset vector distance range from the second object, according to the automatic movement of the second object.

The automatic vector-moving of the second object may include: determining a first control point and a second control point in the second object; and vector-moving the first control point and the second control point along the preset path.

The automatic vector-moving of the second object may include repeatedly moving the second object by a reference distance smaller than the preset vector distance.

The moving of the first object may include moving the first object from a first position to a second position, and the automatic vector-moving of the second object may include: determining that center points of each of the first object and the second object are control points; determining a vector direction between the control points; and straightly moving the second object by a reference distance in the vector direction.

The automatic vector-moving of the second object may include arch-moving the second object by the predetermined distance in the first direction along the preset path.

The plurality of objects may be three-dimensional (3D) objects.

The method for automatically moving an object in a simulation system may further include: extracting intersection points at which the plurality of 3D objects and a reference surface having a plane equation intersect with each other; converting the 3D objects into two-dimensional (2D) objects using the intersection points; and setting a 2D path determined using center points of the 2D objects to the preset path.

The measuring of the vector distance may include calculating a shortest distance between points of the first object and points of the second object in relation to the preset path to obtain the vector distance.

The measuring of the vector distance may include calculating a shortest distance between points of the first object and surfaces of the second object in relation to the preset path to obtain the vector distance.

The method for automatically moving an object in a simulation system may further include: leveling the numbers of points of the first object and the second object; and calculating distances between the points of the first object and the points of the second object depending on levels determined by a user input signal to calculate the shortest distance.

According to another exemplary embodiment of the present invention, a simulation system may include: a display unit displaying a plurality of objects; a memory storing an object distance measuring program for measuring a vector distance between the objects therein; a user input unit generating a movement signal for a first object; and a control unit driving the object distance measuring program stored in the memory to measure a vector distance between the first object and a second object which is an object adjacent to the first object according to movement of the first object, automatically vector-moving the second object by a predetermined distance in a first direction along a preset path so that the vector distance is in a preset vector distance range, and displaying the moved objects on the display unit, when the first object of the plurality of objects moves in the first direction on the basis of the movement signal input through the user input unit.

Advantageous Effects

According to an exemplary embodiment of the present invention having the abovementioned configuration, when one object moves, an adjacent object is automatically aligned in consideration of the intention of the user, and convenience of the user may thus be improved.

BEST MODE

Figure 1:
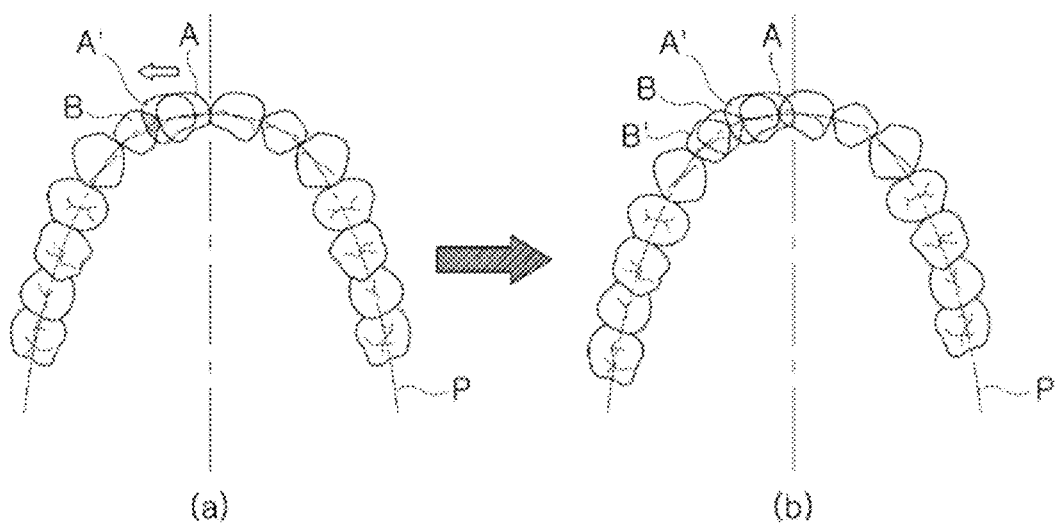
FIGS. 1A and 1B are conceptual diagrams for describing a first example of a method for automatically moving an object in a simulation system according to an exemplary embodiment of the present invention.

Hereinafter, the present invention will be described in more detail through exemplary embodiments that do not limit the present invention with reference to the accompanying drawings, and the same components will be denoted by the same reference numerals in some of the accompanying drawings.

In the present specification, a method for moving teeth in an orthodontic treatment will be mainly described in order to obviously describe the present invention. However, it is to be understood that the present invention is not limited thereto, but may be used in various fields.

Hereinafter, a vector distance means a distance having directivity or a distance having a vector value in order to recognize whether collision is generated between objects or objects are spaced apart from each other.

In addition, vector-movement means movement toward a forward direction or a reverse direction in relation to a preset path.

Further, separation-vector-movement means movement toward a reverse direction in relation to a preset path, that is, movement increasing an interval between objects or separating objects that are in a collision state from each other.

Further, adjacent-vector-movement means movement toward a reverse direction in relation to a preset path, that is, movement decreasing an interval between objects.

FIGS. 1A and 1B are conceptual diagrams for describing a first example of a method for automatically moving an object in a simulation system according to an exemplary embodiment of the present invention. FIGS. 1A and 1B are diagrams for describing movement of a second object when a first object and the second object overlap with each other as the first object moves.

When each of teeth is objectified from a tooth image of a subject obtained through a computerized tomography (CT) scan, an image as illustrated in FIG. 1A is displayed. Here, when a first object A which is a front tooth moves along a preset path P (moves to A'), the first object A' and a second object B adjacent to the first object A' collide (overlap) with each other. Since this may not actually occur, a tooth corresponding to the second object B needs to actually move at the time of an orthodontic treatment. In this case, as illustrated in FIG. 1B, the second object B moves along the preset path P by a predetermined distance (moves to B'), the collision may be avoided.

Here, the preset path P may be created on the basis of standard dental arch data pre-stored in a memory, be created through a dental arch image in the tooth image of the subject, or be created by connecting center points (control points) of the respective objects to each other.

Hereinafter, a processing method in the case in which teeth are spaced apart from each other will be described with reference to FIGS. 2A and 2B.

Figure 2:
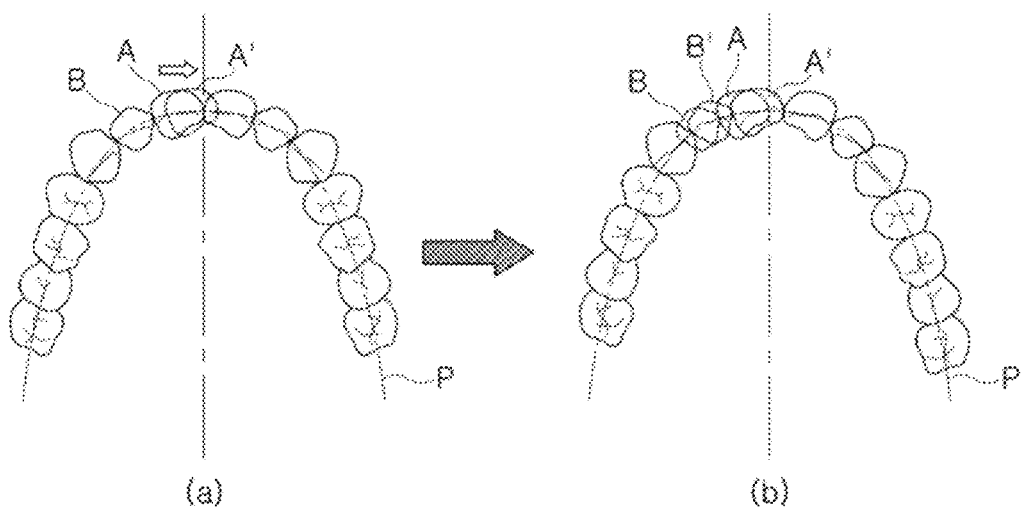
FIGS. 2A and 2B are conceptual diagrams for describing a second example of a method for automatically moving an object in a simulation system according to an exemplary embodiment of the present invention.

FIGS. 2A and 2B are conceptual diagrams for describing a second example of a method for automatically moving an object in a simulation system according to an exemplary embodiment of the present invention. In FIG. 2A, the first object A moves in a direction in which it is spaced apart from the second object B (moves to A'), unlike FIG. 1A. In this case, the second object B vector-adjacent-moves to a preset distance (into a preset vector distance) from the first object A' (moves to B'). Therefore, the respective objects are aligned in parallel with each other with a predetermined interval therebetween. In this case, center points of gravity of the respective objects serve as control points, and these control points move along the preset path P. A movement scheme of the control points will be described above.

Hereinafter, detailed methods through which the method described above is performed will be described in detail below with reference to FIG. 3.

Figure 3:
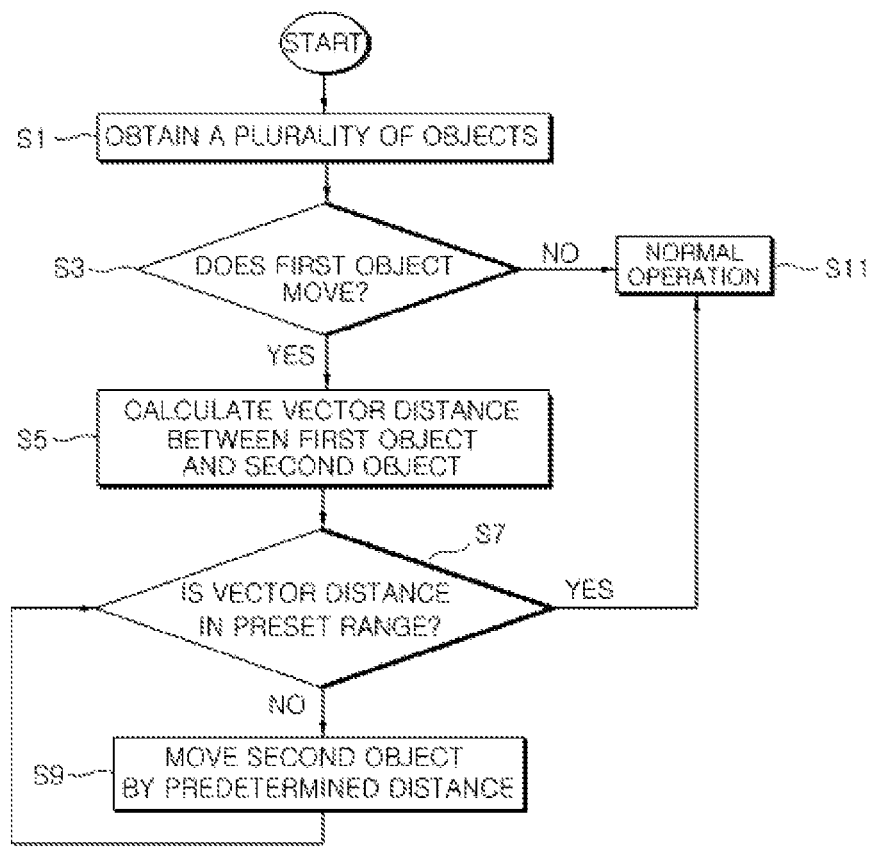
FIG. 3 is a flowchart for describing operations of a method for automatically moving an object in a simulation system according to an exemplary embodiment of the present invention.

FIG. 3 is a flowchart for describing operations of a method for automatically moving an object in a simulation system according to an exemplary embodiment of the present invention. First, a plurality of objects are obtained (S1). Here, each of teeth is objectified from a dental arch image of a subject obtained through a CT scan. Therefore, a plurality of teeth objects are created. Then, a user moves a first object which is one of the plurality of objects in a first direction through a user input unit (S3). That is, the movement of the first object means that the first objects moves from a first position to a second position. In addition, the respective objects may have control points. There is a case in which the control point is a center point of gravity (that is, a case in which the number of control points is one) and there is a case in which two control points (that is, a first control point and a second control point) exist on surfaces of the object. In addition, such a control point may be used as a portion matched to a preset path when the object moves or be used to determine a movement direction of the object. This will be described below. Meanwhile, here, the first direction means a forward direction (a clockwise direction) or a reverse direction (a counterclockwise direction) along the preset path. Then, a vector distance between the first object and a second object which is an object adjacent to the first object is measured (calculated) according to the movement of the first object (S5). Here, the vector distance may be divided into a distance having a plus value (that is, a case in which the first object and the second object are spaced apart from each other) and a distance having a minus value (that is, a case in which the first object and the second object overlap with each other). Then, it is confirmed whether or not the vector distance is in a preset range (that is, whether or not the vector distance is a distance at which the first object and the second object are aligned well with each other). When the vector distance is not in the preset range, the second object automatically vector-moves by a predetermined distance in the first direction along the preset path (S9). Here, the preset path may be set by connecting center points of the plurality of objects to each other or may be a dental arch line of pre-stored standard data.

Meanwhile, the vector-movement will be described in more detail with reference to FIG. 5.

When the vector-movement distance is the minus value, it is decided that the first object and the second object overlap with each other to separation-vector-move the second object along a movement direction of the first object in order to allow the first object and the second object to be in the preset range, and when the vector-movement distance is the plus value, it is decided that the first object and the second object are spaced apart from each other to adjacent-vector-move the second object along the movement direction of the first object in order to allow the first object and the second object to be in a preset vector distance range (S9). Here, in the automatic-vector-movement of the second object, after a vector direction between the control point (the center point) of the first object and the control point (the center point) of the second object is determined, the second object may straightly move by a reference distance in the vector direction. Meanwhile, arch-movement is also possible. That is, the second object may arch-move by a predetermined distance in the first direction which is the movement direction of the first object along the preset path. In addition, in the case in which the second object has two control points, the second object may move while both of the two control points being matched to the preset path. In this case, since the two control points are matched to the preset path, the second object naturally moves and rotates in the preset path and stops at an expected point.

Then, a vector distance between the first object and the second object is again calculated (S5). Such an operation is repeated to allow the vector distance to be within a preset vector distance.

Then, a third object which is another object adjacent to the second object also vector-moves depending on the above-mentioned step, according to the movement of the second object. That is, the third object which is the object adjacent to the second object automatically moves so that the third object is in the preset vector distance range from the second object, according to the automatic movement of the second object. Such a process is performed on all the objects, such that all the objects are automatically aligned with one another on the preset path, according to the movement of the first object.

Here, each object moves by a reference distance smaller than the preset vector distance. This will be described in more detail with reference to FIG. 5.

Meanwhile, in the present invention, the objects are three-dimensional (3D) objects. Therefore, a calculation amount is large, and a countermeasure is thus required. Therefore, in the present invention, the plurality of objects which are the 3D objects are converted into two-dimensional (2D) objects using a plane equation. That is, intersection points at which the plurality of 3D objects and a reference surface having the plane equation intersect with each other are extracted, the 3D objects are converted into the 2D objects using the intersection points, and a 2D path determined using center points of the 2D objects is set to the preset path, thereby making it possible to simply set the preset path. In addition, an automatic movement process of the second objects may be performed after the 3D objects are converted into the 2D objects. In this case, after all the automatic aligning processes are finished using the 2D objects, the 2D objects may again return to 3D objects using the plane equation. Since movement and a position change are two-dimensionally performed under a 3D environment through the abovementioned processes, a work speed may be improved.

Figure 4:
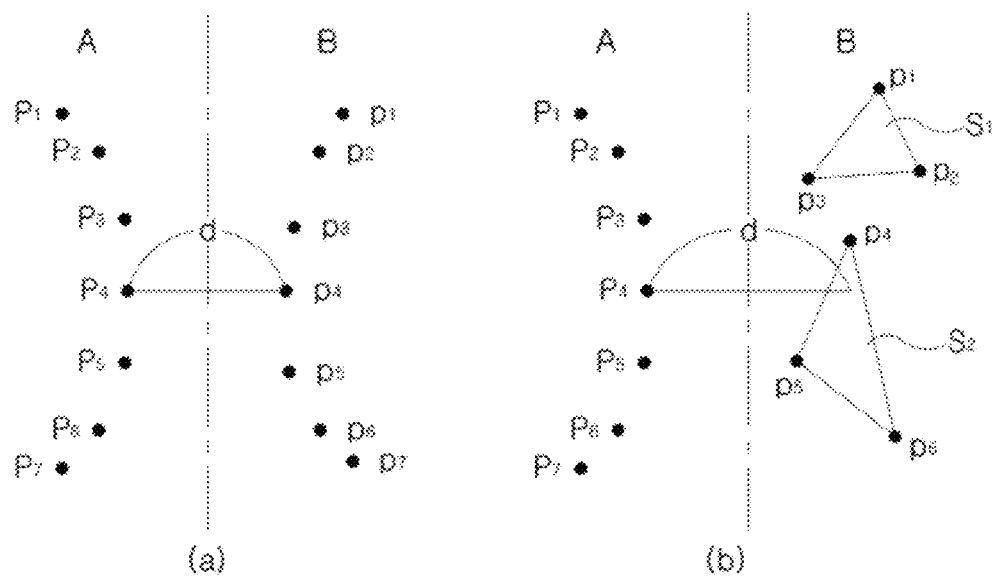
FIGS. 4A and 4B are conceptual diagrams illustrating a method for measuring a vector distance in the method for automatically moving an object in a simulation system according to an exemplary embodiment of the present invention.

Hereinafter, a method for measuring the vector distance between the first object and the second object which is the object adjacent to the first object will be described with reference to FIGS. 4A and 4B.

FIGS. 4A and 4B are conceptual diagrams illustrating a method for measuring a vector distance in the method for automatically moving an object in a simulation system according to an exemplary embodiment of the present invention. In FIGS. 4A and 4B, A means a first object, and B means a second object. The first object and the second object are 2D or 3D objects consisting of a plurality of points. As a method for measuring a distance between A and B, there is a method for measuring distances between points of A and points of B in a state in which a direction from A toward B is set to a positive direction. According to such a method, distances between all the points P1 to P7 of A and all the point p1 to p7 of B are measured, and the shortest distance d of the measured distances is defined as a vector distance. In FIG. 4B, a method for measuring distances between points and surfaces is illustrated. Distances between all the points P1 to P7 in A which is the first object and a plurality of surfaces S1 and S2 consisting of three points in B which is the second object are measured, and the shortest distance of the measured distances is defined as a vector distance.

Meanwhile, although not illustrated, distances between surfaces in A which is the first object and points in B which is the second object are measured, and the shortest distance of the measured distances may be defined as a vector distance. This is a case opposed to that of FIG. 4B.

In FIGS. 4A and 4B, in a state in the first object and the second object are spaced apart from each other, the vector distance has a plus value. It is to be understood that when the first object and the second object overlap with each other, the vector distance has a minus value.

Meanwhile, the numbers of points of the first object and the second object may be leveled in order to raise a calculation speed. For example, a case in which the number of points of the first object is determined to be 100 may be set to level 1, a case in which the number of points of the first object is determined to be 1000 may be set to level 2, a case in which the number of points of the first object is determined to be 10000 may be set to level 3, and a case in which the number of points of the first object is determined to be 100000 may be set to level 4.

In the case in which a user selects level 1 and then performs the automatic movement of the second object, a calculation speed is very high, but accuracy is low.

On the other hand, in the case in which the user selects level 4 and then performs the automatic movement of the second object, a calculation speed is very low, but accuracy is most excellent.

Hereinafter, a movement method of the second object will be described with reference to FIG. 5.

Figure 5:
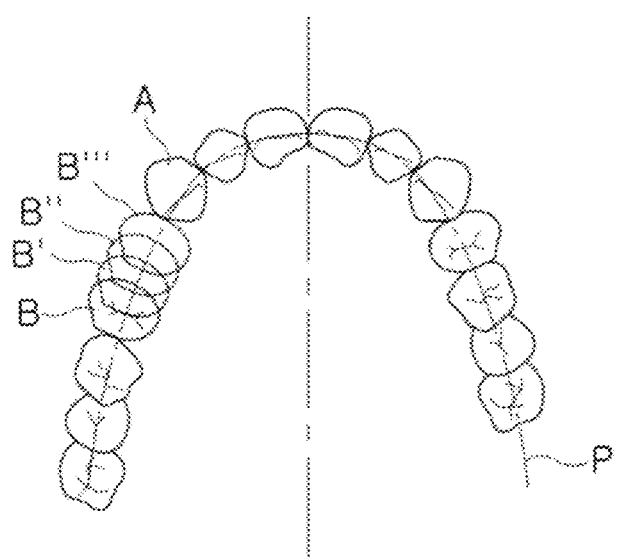
FIG. 5 is a conceptual diagram for describing a method for performing vector-movement in the method for automatically moving an object in a simulation system according to an exemplary embodiment of the present invention.

FIG. 5 is a conceptual diagram for describing a method for performing vector-movement in the method for automatically moving an object in a simulation system according to an exemplary embodiment of the present invention. An example illustrated in FIG. 5 is a case in which the first object moves in a spaced direction, that is, a case in which the first object moves in a direction in which the first object and the second object become distant from each other. In this case, the second object repeats movement by a predetermined distance, as described with reference to FIG. 3. Here, the predetermined distance needs to be smaller than the vector movement distance. Particularly, the predetermined distance is significantly related to accuracy of automatic alignment in the present invention. The smaller the repeated predetermined distance, the higher the accuracy of the automatic alignment, but the larger the calculation burden. In FIG. 5, a form in which the second object moves to B', B", and B''' is illustrated. As described above, the second object repeatedly moves several times by a small distance to be automatically aligned.

Hereinafter, a simulation system according to an exemplary embodiment of the present invention performing the abovementioned operations will be described in detail with reference to FIG. 6.

Figure 6:
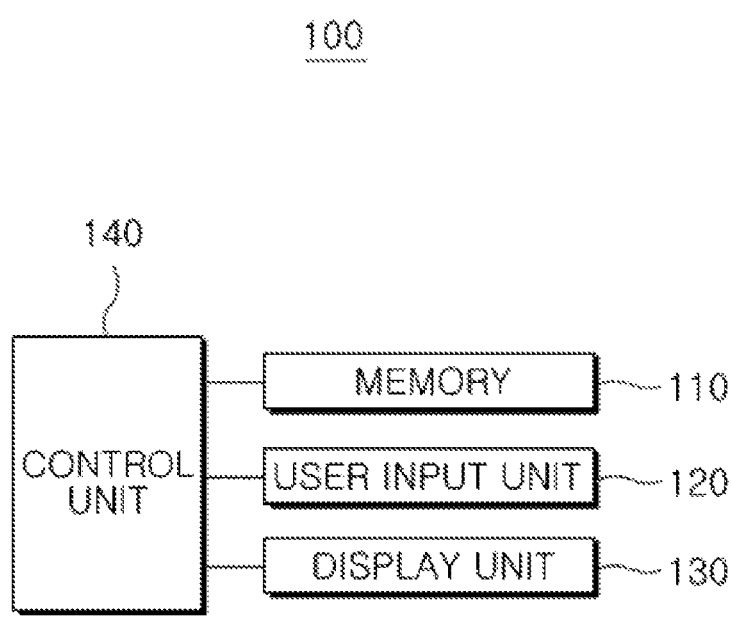
FIG. 6 is a block diagram for describing electronic components of a simulation system according to an exemplary embodiment of the present invention.

FIG. 6 is a block diagram for describing electronic components of a simulation system according to another exemplary embodiment of the present invention. As illustrated in FIG. 6, the simulation system 100 according to an exemplary embodiment of the present invention may be configured to include a memory 110, a user input unit 120, a display unit 130, and a control unit 140.

The memory 110 is a component in which an object distance measuring program for measuring a vector distance between objects is stored. The memory 110 may include at least one of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

The user input unit 120 is a component for generating a movement signal for the first object. A key button, a mouse, a keyboard, a touch screen, or the like, may be used as the user input unit 120.

The display unit 130 displays (outputs) information processed by the control unit of the simulation system according to the present invention. That is, the display unit is a component for displaying teeth which are objects and various kinds of graphic user interface (GUI) and user interface (UI) information related to the teeth.

The display unit 130 may include at least one of a liquid crystal display (LCD), a thin film transistor-liquid crystal display (TFT LCD), an organic light-emitting diode (OLED), a flexible display, and a 3D display.

The control unit 140 serves to drive the object distance measuring program stored in the memory 110 to measure the vector distance between the first object and the second object which is the object adjacent to the first object according to the movement of the first object, automatically vector-move the second object by the predetermined distance in the first direction along the preset path so that the vector distance is in the preset vector distance range, and display the moved objectsm on the display unit 130, when the first object of the plurality of objects moves in the first direction on the basis of the movement signal input through the user input unit 120. Since operations of the control unit have been described in detail with reference to FIGS. 3 to 5, a description therefor will be omitted for simplification.

In addition, according to an exemplary embodiment of the present invention, the abovementioned method may be implemented as a processor-readable code in a medium in which a program is recorded. That is, a method for automatically controlling a tooth protrusion angle in the abovementioned orthodontic treatment simulation apparatus may be stored in a computer-readable recording medium. An example of a processor-readable medium may include a read only memory (ROM), a random access memory (RAM), a compact disk read only memory (CD-ROM), a magnetic tape, a floppy disk, an optical data storage, or the like, and also include a medium implemented in a form of a carrier wave (for example, transmission through the Internet).

According to an exemplary embodiment of the present invention having the abovementioned configuration, when one object moves, an adjacent object is automatically aligned in consideration of the intention of the user, and convenience of the user may thus be improved.

In the method for automatically moving an object in a simulation system and the simulation system using the same as described above, the configurations and the methods according to the exemplary embodiments described above are not restrictively limited, and all or some of the respective exemplary embodiments may be selectively combined with one another so that various modifications of the exemplary embodiments may be made.

The invention claimed is:

1. A method for automatically moving an object in a simulation system, comprising:
    moving a first object of a plurality of objects using a user input unit from a first position to a second position in a first direction in accordance with a predetermined dental arch path, the plurality of objects being obtained from a dental arch image of a subject by a control unit and being three-dimensional (3D) objects;
    measuring a vector distance between the first object and a second object which is adjacent to the first object based on an expected movement of the first object by a control unit;
    based on the vector distance, automatically vector-moving the second object that is adjacent to the first object, in the simulation system, by a predetermined distance in the first direction along the predetermined dental arch path until the vector distance between the first object and the second object is in a preset vector distance range by the control unit, thereby resulting in automatic alignment of the plurality of objects with one another on the predetermined dental arch path, automatically moving a third object which is an object adjacent to the second object so that the third object is in the preset vector distance range from the second object by the control unit according to the automatic movement of the second object, extracting intersection points at which the plurality of 3D objects and a reference surface having a plane equation intersect with each other by the control unit, converting the 3D objects into two-dimensional (2D) objects using the intersection points by the control unit, and setting a 2D path which is determined using center points of the 2D objects to the present path by the control unit, wherein the predetermined distance is smaller than the vector distance and wherein the automatic vector-moving of the second object includes, based on the vector distance, determining whether the first object and the second object either overlap with or spaced apart from each other.

2. The method for automatically moving an object in a simulation system of claim 1, wherein the automatic vector-moving of the second object includes:

deciding that the first object and the second object overlap with each other and separation-vector moving the second object along a movement direction of the first object in order to allow the first object and the second object to be disposed in a preset range by the control unit, when the vector distance is a minus value.

3. The method for automatically moving an object in a simulation system of claim 1, wherein the automatic vector-moving of the second object includes:

deciding that the first object and the second object are spaced apart from each other and adjacent-vector moving the second object along a movement direction of the first object in order to allow the first object and the second object to be disposed in the present vector distance range by the control unit, when the vector distance is a plus value.

4. The method for automatically moving an object in a simulation system of claim 1, wherein the automatic vector-moving of the second object includes:

determining a first control point and a second control point in the second object by the control unit; and vector-moving the first control point and the second control point along the preset path by the control unit.

5. The method for automatically moving an object in a simulation system of claim 1, wherein the automatic vector-moving of the second object further includes:

repeatedly moving the second object by a reference distance smaller than the preset vector distance by the control unit.

6. The method for automatically moving an object in a simulation system of claim 1, wherein the automatic vector-moving of the second object includes:

determining that center points of each of the first object and the second object are control points by the control unit;

determining a vector direction between the control points by the control unit; and straightly moving the second object by a reference distance in the vector direction by the control unit.

7. The method for automatically moving an object in a simulation system of claim 1, wherein the automatic vector-moving of the second object includes: moving the second object in an arch shape direction in accordance with the predetermined dental arch path by the predetermined distance in the first direction along the preset path.

8. The method for automatically moving an object in a simulation system of claim 1, wherein the measuring of the vector distance includes calculating a shortest distance between points of the first object and points of the second object in relation to the preset path to obtain the vector distance by the control unit.

9. The method for automatically moving an object in a simulation system of claim 1, wherein the measuring of the vector distance includes calculating a shortest distance between points of the first object and surfaces of the second object in relation to the preset path to obtain the vector distance by the control unit.

10. The method for automatically moving an object in a simulation system of claim 8, further comprising:

leveling the numbers of points of the first object and the second object by the control unit; and calculating distance between the points of the first object and the points of the second object depending on levels determined by a user input signal to calculate the shortest distance by the control unit.

11. A simulation system for a dental application comprising:

a display unit configured to display a plurality of objects, the plurality of objects being obtained from a dental arch image of a subject and being three-dimensional (3D) objects;

a memory configured to store an object distance measuring program for measuring a vector distance between the objects;

a user input unit configured to generate a movement signal for a first object of the plurality of objects; and a control unit configured to:

execute the object distance measuring program stored in the memory to measure a vector distance between the first object and a second object which is adjacent to the first object based on an expected movement of the first object, based on the vector distance, automatically vector-move the second object that is adjacent to the first object, in the simulation system, by a predetermined distance in a first direction along a predetermined dental arch path until the vector distance between the first object and the second object is in a preset vector distance range, thereby resulting in automatic alignment of the plurality of objects with one another on the predetermined dental arch path, automatically move a third object which is an object adjacent to the second object so that the third object is in the preset vector distance range from the second object by the control unit according to the automatic movement of the second object, extract intersection points at which the plurality of 3D objects and a reference surface having a plane equation intersect with each other by the control unit, convert the 3D objects into two-dimensional (2D) objects using the intersection points by the control unit, and set a 2D path that is determined using center points of the 2D objects to the present path by the control unit, wherein the predetermined distance is smaller than the vector distance, and display the moved objects on the display unit, when the first object of the plurality of objects moves in the first direction based on the movement signal input through the user input unit and wherein the automatic vector-moving of the second object includes, based on the vector distance, determining whether the first object and the second object either overlap with or spaced apart from each other.

12. A non-transitory computer-readable recording medium in which the method for automatically moving an object in a simulation system of claim 1 is stored.

\* \* \* \* \*